US012588806B2

(12) United States Patent
Johnsen et al.

(10) Patent No.: US 12,588,806 B2
(45) Date of Patent: Mar. 31, 2026

(54) TIP HOUSING FOR AN ENDOSCOPE WITH A COATED WALL SURFACE

(71) Applicant: AMBU A/S, Ballerup (DK)

(72) Inventors: Lasse Markworth Johnsen, Birkerød (DK); Morten Sørensen, Ballerup (DK); Christian Lachenmeier, København N (DK); Irene Rivas Palacios, Kongens Lyngby (DK)

(73) Assignee: AMBU A/S, Ballerup (DK)

( * ) Notice: Subject to any disclaimer, the term of this patent is extended or adjusted under 35 U.S.C. 154(b) by 674 days.

(21) Appl. No.: 17/786,489

(22) PCT Filed: Nov. 20, 2020

(86) PCT No.: PCT/EP2020/082948
§ 371 (c)(1),
(2) Date: Jun. 16, 2022

(87) PCT Pub. No.: WO2021/121872
PCT Pub. Date: Jun. 24, 2021

(65) Prior Publication Data
US 2023/0038606 A1 Feb. 9, 2023

(30) Foreign Application Priority Data

Dec. 19, 2019 (EP) .................................... 19218156

(51) Int. Cl.
*A61B 1/06* (2006.01)
*A61B 1/00* (2006.01)
(52) U.S. Cl.
CPC .......... *A61B 1/0684* (2013.01); *A61B 1/0008* (2013.01); *A61B 1/0011* (2013.01)
(58) Field of Classification Search
None
See application file for complete search history.

(56) References Cited

U.S. PATENT DOCUMENTS 5,193,525 A 3/1993 Silverstein et al.
8,029,438 B2 10/2011 Hagihara et al.
(Continued)

FOREIGN PATENT DOCUMENTS

EP 2266452 A2 12/2010
EP 3222749 A1 9/2017
(Continued)

OTHER PUBLICATIONS

International Search Report and Written Opinion in PCT/EP2020/082948 dated Feb. 8, 2021, 14 pages.
(Continued)

*Primary Examiner* — Alison L Hindenlang
*Assistant Examiner* — Debjani Roy
(74) *Attorney, Agent, or Firm* — Faegre Drinker Biddle & Reath LLP

(57) ABSTRACT
A method for manufacturing an endoscope having a tip housing may comprise the steps of moulding at least one tip housing for an endoscope by injection moulding or by multi shot injection moulding. Each tip housing may comprise an integrally formed wall defining an interior cavity and a proximal opening providing access to the interior cavity. The wall may comprise a longitudinally extending side wall portion, a distal end wall portion, and a window portion. The window portion may consist essentially of a transparent first material and form part of the side wall portion and/or the distal end wall portion. The wall may further comprise a wall surface facing the exterior of the tip housing and having a window surface of the window portion and a distally facing end surface of the distal end wall portion. The method may further comprise positioning the at least one tip housing in a treatment chamber; and applying, in the treatment chamber, a treatment formulation to provide a coating on at least the wall surface.

13 Claims, 7 Drawing Sheets

(56) References Cited

U.S. PATENT DOCUMENTS

| | | | |
|---|---|---|---|
| 8,381,728 | B2 | 2/2013 | Rao et al. |
| 9,060,677 | B2 | 6/2015 | Imai |
| 9,125,582 | B2 | 9/2015 | Petersen |
| 10,321,804 | B2 | 6/2019 | Jacobsen et al. |
| 12,053,152 | B2 | 8/2024 | Sørensen et al. |
| 2002/0026145 | A1 | 2/2002 | Bagaoisan et al. |
| 2005/0136217 | A1 | 6/2005 | Barthlott et al. |
| 2005/0239294 | A1 | 10/2005 | Rosenblum et al. |
| 2006/0161048 | A1 | 7/2006 | Squicciarini |
| 2008/0078386 | A1 | 4/2008 | Feldhahn et al. |
| 2008/0214895 | A1* | 9/2008 | Campos ................. A61B 1/307 |
| | | | 600/129 |
| 2008/0228035 | A1 | 9/2008 | Hagihara et al. |
| 2010/0275838 | A1* | 11/2010 | Pei ....................... C23C 14/568 |
| | | | 118/500 |
| 2011/0252899 | A1* | 10/2011 | Felts .................... C23C 16/458 |
| | | | 118/712 |
| 2011/0270221 | A1 | 11/2011 | Ross |
| 2013/0175720 | A1* | 7/2013 | Otsuka ................... B29C 45/16 |
| | | | 264/1.32 |
| 2013/0266761 | A1 | 10/2013 | Ho et al. |
| 2013/0338436 | A1* | 12/2013 | Dresher ............ A61B 1/00096 |
| | | | 600/109 |
| 2014/0182587 | A1 | 7/2014 | Dunne et al. |
| 2014/0200466 | A1 | 7/2014 | Sereno et al. |
| 2014/0275786 | A1 | 9/2014 | Goto et al. |
| 2014/0276407 | A1 | 9/2014 | DeVries et al. |
| 2014/0277082 | A1 | 9/2014 | Janardhan et al. |
| 2014/0295053 | A1* | 10/2014 | Felts .................... C23C 16/505 |
| | | | 118/723 R |
| 2014/0318657 | A1 | 10/2014 | Bixler et al. |
| 2015/0142041 | A1 | 5/2015 | Kendale et al. |
| 2015/0251201 | A1 | 9/2015 | Hradetzky et al. |
| 2015/0289751 | A1 | 10/2015 | Frerck et al. |
| 2015/0306813 | A1 | 10/2015 | Roehrig et al. |
| 2016/0229095 | A1 | 8/2016 | Mori et al. |
| 2016/0270631 | A1 | 9/2016 | Kirma et al. |
| 2017/0095242 | A1 | 4/2017 | Milbocker et al. |
| 2017/0146453 | A1 | 5/2017 | Giles et al. |
| 2019/0016084 | A1 | 1/2019 | Hayashi et al. |
| 2019/0282070 | A1 | 9/2019 | Vilhelmsen et al. |
| 2019/0328299 | A1 | 10/2019 | Felts et al. |
| 2020/0172740 | A1* | 6/2020 | Ou ....................... C09D 183/04 |

FOREIGN PATENT DOCUMENTS

| | | |
|---|---|---|
| EP | 3329955 A1 | 6/2018 |
| EP | 3539449 A1 | 9/2019 |
| JP | H07-275185 A | 10/1995 |
| JP | 2006-055275 A | 3/2006 |
| JP | 2010-051696 A | 3/2010 |
| JP | 2017-046854 A | 3/2017 |
| WO | 2010/066790 A1 | 6/2010 |
| WO | 2014/071010 A1 | 5/2014 |
| WO | 2014/106511 A1 | 7/2014 |
| WO | 2017/189855 A1 | 11/2017 |

OTHER PUBLICATIONS

Extended European Search Report in European patent application No. 19218156.8 dated Jun. 6, 2020, 9 pages.
Examination Report issued in EP 19218156.8, dated Jun. 27, 2023, 13 pages.
Examination Report issued in EP 19218156.8, dated Apr. 17, 2025, 8 pages.

* cited by examiner

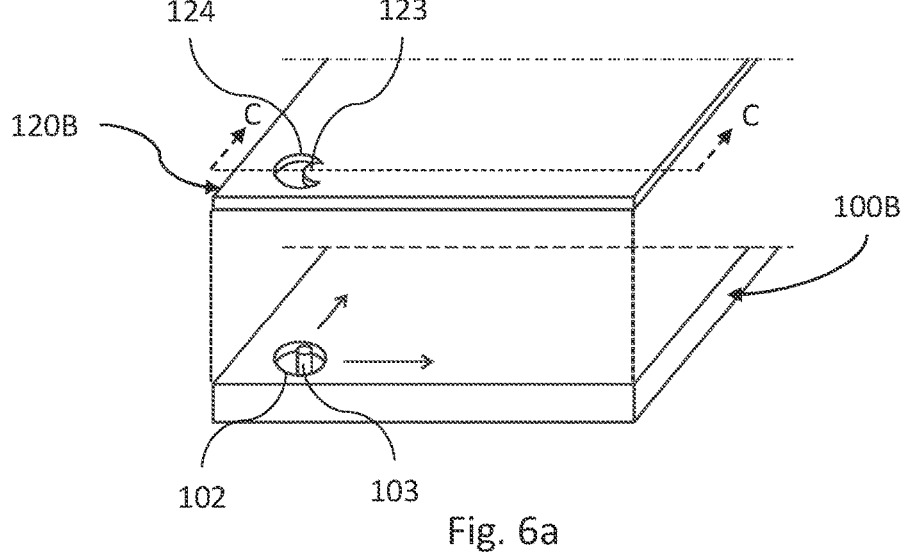
Fig. 6a
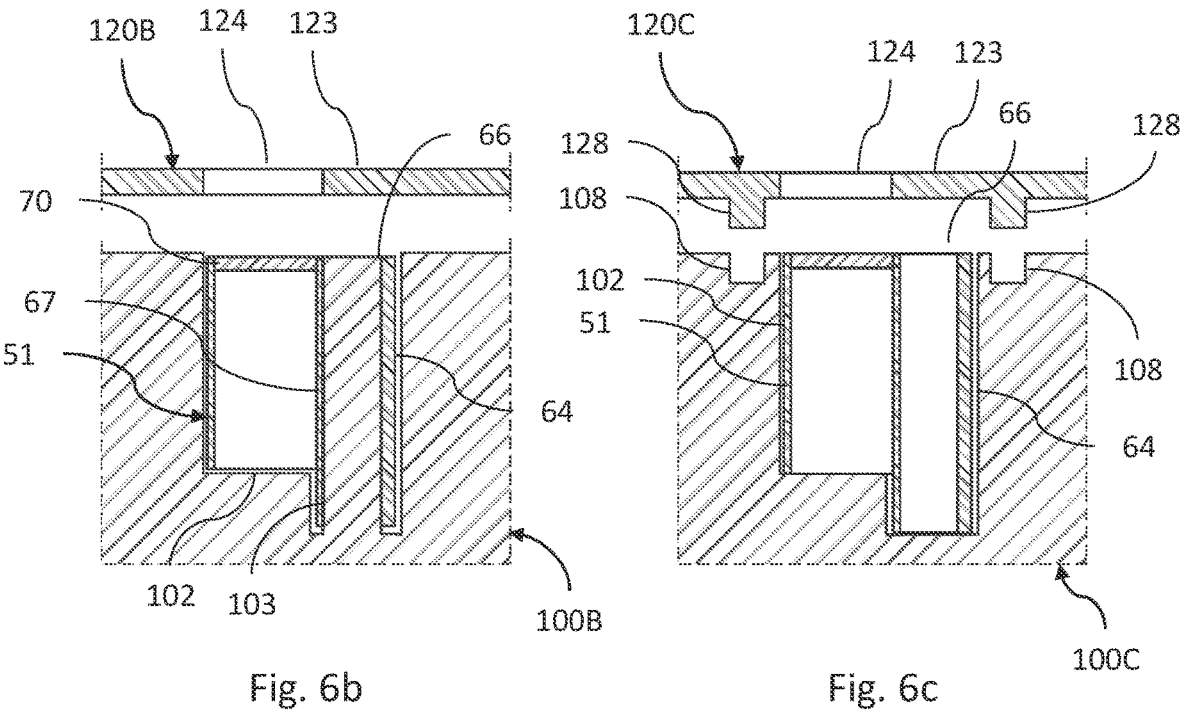
Fig. 6b                   Fig. 6c

TIP HOUSING FOR AN ENDOSCOPE WITH A COATED WALL SURFACE

CROSS-REFERENCE TO PRIOR APPLICATION

This application is a § 371 National Stage Application of PCT International Application No. PCT/EP2020/082948 filed Nov. 20, 2020, which claims the priority of European Patent Application No. 19218156.8, filed Dec. 19, 2019, each of which are herein incorporated by reference in their entirety.

TECHNICAL FIELD

The present disclosure relates to a tip housing for an endoscope and a method of manufacturing such a tip housing for an endoscope.

BACKGROUND

Vision devices, such endotracheal tubes and insertion endoscopes are well-known devices in the medical field for visually examining the interior of a hollow organ or cavity of a body, such as lungs, by means of inserting an insertion tube of the endoscope with a handle at the proximal end as seen from the operator, and visual inspections means, such as a built-in camera, at the distal end of the elongated insertion tube. This therefore normally requires illumination of the area in front of the distal tip of the endoscope, in particular the field of vision of the camera(s). One known way of achieving such illumination is to incorporate one or more Light Emitting Diodes (LEDs) in the tip of the endoscope, e.g. as mentioned in WO2014/106511 disclosing a disposable endoscope. Instead of using a camera, endoscopes may also be fibre-optical, in which case the optical fibres run along inside of the elongated insertion tube to the tip part. Electrical wiring for the camera and other electronics such as LED lighting accommodated in the tip part at the distal end run along the inside of the elongated insertion tube from the handle to the tip part.

In order to be able to manoeuvre the endoscope inside the body cavity, the distal end of the endoscope may comprise a bending section with increased flexibility, e.g. a number of articulated segments of which the tip part forms the distal-most segment. This is typically done by tensioning or slacking pull wires also running along the inside of the elongated insertion tube from the tip part through the remainder of articulated segments to a control mechanism, such as a control lever, of the handle. Furthermore, a working channel may run along the inside of the insertion tube from the handle to the tip part, e.g. allowing liquid to be removed from the body cavity or allowing the insertion of medical tools or surgical instruments into the body cavity.

When, as in the present invention, the insertion tube of the endoscope is intended to be inserted into a human body cavity, the insertion tube needs to be sealed in a watertight manner. This is particularly true for the distal tip part because it accommodates the camera, LED(s) and other delicate electronics, prone to malfunction or destruction if exposed to humidity.

One known way of sealing the tip part of an endoscope is disclosed in WO2010/066790. In this document a transparent monolithic housing is formed around the electronics and working channel by placing the electronics and the tube forming the working channel in a mould of transparent material, such as silicone. A transparent UV-curable resin is then inserted from the bottom of the mould to avoid bubbles forming in the transparent resin. Because the resin rises slowly from the bottom, the air is slowly expelled from top of the mould without any risk of air bubbles being trapped in the mould. The resin is then cured using UV irradiation through the transparent mould to form the monolithic housing. However, forming a monolithic housing in this way has some drawbacks. One is that it is a rather slow process. Another is that it can be difficult to position and maintain the components precisely in position during the insertion of the resin. Thus, in few cases, the camera or LEDs may be off-set sideways, or a thin transparent layer may inadvertently be created in front of the camera and/or LEDs, thereby reducing the imaging qualities of the tip part. This will lead to the product being discarded in the quality control, thereby increasing overall cost of manufacturing.

In recent years, disposable endoscopes have been developed to include an integrally moulded tip housing of the distal tip, e.g. as disclosed in EP3539449, defining an interior cavity accommodating a camera which looks through a window of the tip housing. A proximal end of the tip housing is typically adhesively sealed to provide a watertight cavity for the electronics of the distal tip, which is then connected to the insertion tube extending to the handle of the endoscope. The exterior surface of the tip housing is exposed to a variety of bodily secretions during endoscopy which can decrease the optical performance of the camera. To enable such endoscopes for performing more medical procedures, the outer diameter of the entire insertion tube including the tip housing has been miniaturised which has pushed moulding techniques to the limit due the reduced wall thickness of tip housing.

SUMMARY

In light of the above, it may be seen as an object of the present disclosure to provide a tip housing for an endoscope with improved optical properties during use.

One or more of these objects may be met by aspects of the present disclosure as described in the following.

A first aspect of this disclosure relates to a tip housing for an endoscope, the tip housing comprising an integrally formed wall or an integrally moulded wall defining an interior cavity and a proximal opening providing access to the interior cavity, the wall comprising:

a longitudinally extending side wall portion, a distal end wall portion, and a window portion consisting essentially of a transparent first material and forming part of the side wall portion and/or the distal end wall portion; and a wall surface facing the exterior of the tip housing and having a window surface of the window portion and a distally facing end surface of the distal end wall portion;

wherein the tip housing comprises a coating provided at least on the wall surface, the coating being one or more selected from the group consisting of:

a transparent coating;
a hydrophobic coating;
an oleophobic coating;
a hydrophilic coating;
an oleophilic coating; and
an optical coating, such as a notch filter coating, an infrared filter coating, an antireflection coating, and/or a low/high/band pass filter coating.

Such a tip housing may be advantageous in that the coating is provided on the wall surface which allows tailoring the surface characteristic of this critical surface to suit the needs of the specific endoscopy application.

A hydro- and/or oleophobic coating may be particularly advantageous for endoscopic applications in relatively dry bodily cavities, such as bronchoscopy.

A hydro- and/or oleophilic coating may be particularly advantageous for endoscopic applications in relatively wet bodily cavities, such as, cystoscopy, ureteroscopy, or hysteroscopy.

Additionally in some embodiments, the coating may be hydrophobic and oleophobic. Additionally, the coating may be transparent. Additionally, the coating may be an optical filter.

Alternatively in some embodiments, the coating may be hydrophilic and oleophilic. Additionally, the coating may be transparent. Additionally, the coating may be an optical filter.

In this disclosure, a transparent coating may be understood as a coating permitting the passing of at least 80%, 85%, 90%, 95%, 99%, or 99.9% of the light intensity through the coating. A transparent coating may improve the optical performance of the camera.

In this disclosure, an optical coating may be understood as a coating altering one or more optical properties of a surface with the optical coating relative to the same surface without the optical coating. Optical properties may include notch or band pass/stop filtering, infrared filtering, antireflection, and/or high/low pass filtering. An optical coating may for instance filter unwanted frequencies, thereby increasing the optical performance of the camera.

In this disclosure, a hydrophobic coating may be understood as a coating decreasing the attraction to water of a surface with the hydrophobic coating relative to the same surface without the hydrophobic coating, e.g. by increasing the contact surface angle of a water droplet on a surface with the hydrophobic coating relative to the same surface without the hydrophobic coating. A hydrophobic coating may resist liquid sticking onto the wall surface thereby increases the optical performance of the camera. A hydrophilic coating may be understood as a coating with opposite properties of a hydrophobic coating. The surface contact angle may be measured on this scale using an optical tensiometer.

In this disclosure, an oleophobic coating may be understood as a coating decreasing the attraction to oils of a surface with the oleophobic coating relative to the same surface without the oleophobic coating. An oleophobic coating may resist oil or fats sticking onto the wall surface thereby increasing the optical performance of the camera. An oleophilic coating may be understood as a coating with opposite properties of an oleophobic coating. The surface contact angle may be measured on this scale using an optical tensiometer.

This disclosure also relates to a method of assessing the hydrophobicity or the oleophobicity of a tip housing according to the first aspect of this disclosure comprising the steps of: providing a container with a predetermined amount of water or oil, respectively, then submerging a predetermined number of coated tip housings, then removing the predetermined number of coated tip housings from the container, and then measuring the remaining amount of water or oil, finally comparing the result with the result of the method performed with the same predetermined number of corresponding uncoated tip housings. If more water or oil is removed from the container by means of the coated tip housings compared to the uncoated tip housings, then the coated tip housings exhibit greater hydrophobicity or oleophobicity, respectively. This method may also be used to compare tip housings having a first type of coating with tip housings having a second different type of coating.

Additionally or alternatively, the window portion may be continuous or may be divided into separate transparent portions. The window surface may comprise a camera window surface configured to be positioned in front of a camera allowing the camera to look through a camera window surface, and one or more illumination window surfaces, e.g. a first and second illumination window surface, configured to be positioned in front of one or more light sources, respectively, e.g. a first and a second light source, such as LEDs, allowing the one or more light sources to provide illumination for the camera through the one or more illumination window surfaces. The window portion may comprise one or more internal illumination surfaces positioned opposite of the illumination window surfaces and an internal camera surface positioned opposite of the camera window surface. The coating may be provided on at least the entire camera window surface and optionally on the one or more illumination surfaces. This allows for a specific advantageous coating to be applied to the camera window surface or illumination surfaces but not to other parts of the window surface.

Additionally or alternatively, the coating may be provided on at least the window surface. This may provide the advantage of allowing tailoring of the surface characteristics of the window surface to suit the needs of the specific endoscopy application. Coating on the window surface is advantageous for all the coatings of the first aspect.

Additionally or alternatively, the coating may not be provided on the window surface, in particular the camera window surface. This may be a particularly simple way of achieving most of the advantages of the coating, in particular either the hydrophobic and/or oleophobic coating, or the hydrophilic and/or oleophilic coating.

Additionally or alternatively, the coating may be a first coating and tip housing may comprise a second, different coating provided prior to the first coating. The second coating may be provided on the one or more illumination window surfaces and/or the one or more internal illumination surfaces while other surfaces of the window portion may be screened to prevent the second coating from being applied to these other surfaces. The second coating may be a transmission scattering coating which may provide wide angle transmission scattering and/or narrow area transmission scattering. The amount of scattering may be measured by BS EN ISO 13468 using a hazemeter.

Additionally or alternatively, the tip housing may be formed of separate elements, e.g. a side wall portion and a distal end wall portion, which may include the window portion and in particular the camera window portion. The side wall portion and/or the distal end wall portion may be coated prior to assembly with the remaining elements of the tip housing.

Additionally or alternatively, the wall may comprise or consist essentially of the first transparent material and a second material, which is different from the first material. By providing the tip housing in two different materials, the material choice may be tailored to the purpose of the specific wall portion. The wall may be shaped or manufactured by a multi shot injection moulding process, in particular a two shot or component injection moulding process. The second material may be opaque. Such a wall may provide the advantage that the border between the two different materials is formed in a liquid tight way obviating the need for additional sealing of the border.

Additionally or alternatively, the coating may comprise or consist essentially of one or more selected from the group consisting of: silica-oxide, aluminum oxide, fluorocarbon, polytetrafluoroethylene (PTFE), perfluorosilane and poly(p-xylylene). These compounds may be particularly advantageous for this purpose.

Additionally or alternatively, the coating may be applied by a vapor deposition process. Vapor deposition processes can generally be divided into chemical vapor deposition and physical vapor deposition. Chemical vapor deposition processes include conventional chemical vapor deposition but are preferably a plasma-enhanced or a low-pressure chemical vapor deposition process, since these can work at lower temperatures which is advantageous for coating the tip housing. Chemical vapor deposition processes typically coat every surface exposed to the treatment chamber. Plasma-enhanced chemical vapor deposition works at relatively low temperatures, i.e. in a range of 80 degrees Celsius to 400 degrees Celsius and is thus particularly suited for coating the polymer tip housing. Physical vapor deposition processes are preferably thermal evaporation or sputtering. Physical vapor deposition processes typically only coat surfaces within line of sight. Thermal evaporation physical vapor deposition works in a temperature range of 200 to 600 degrees Celsius, while sputtering physical vapor deposition works at around 300 degrees Celsius. However the temperature of the substrate (i.e. the tip housing) may be much lower, such as around 60 degrees Celsius.

Additionally or alternatively, the treatment formulation may comprise HMDSO, the coating may be fluorocarbon, and be applied by a plasma vapor deposition process.

Additionally or alternatively, the coating may comprise perfluorosilane and be applied by a chemical vapor deposition process.

Additionally or alternatively, the window portion may form part of the distal end wall portion so that the window surface is distally facing. This arrangement of the window portion may be advantageous for coating since the distal end wall is a well-defined area.

Additionally or alternatively, the coating is provided at least on the entire end surface of the distal end wall portion. Coating the entire distal end surface may be advantageous since the distal end wall is a well-defined area.

Additionally or alternatively, the coating may be provided at least on the entire window surface and/or at least on the entire wall surface.

Additionally or alternatively, the wall surface may comprise a side wall surface arranged exterior of the side wall portion, and the coating may not be provided on a proximal portion of the side wall surface. The proximal portion may be opposite of the distal end wall. The proximal portion may extend at least 5%, 10%, 15%, 20%, 25%, 30%, 35%, 40%, 45%, 50%, 55%, 60%, 65%, 70%, 75%, or 80% of the longitudinal extent of the side wall portion. This may be advantageous for adhesively joining the proximal end of the tip housing to an insertion tube.

Additionally or alternatively, the tip housing may comprise a tip working channel portion extending between a proximal entrance at a proximal end of the tip housing and a distal entrance at a distal end of the tip housing. The tip housing may comprise a partition wall separating the tip working channel portion from the interior cavity. The coating may be provided on a distal portion of an inner surface of the working channel. This may provide a better working channel performance e.g. since it may thus be secretion resistant.

Additionally or alternatively, the coating may have a thickness in the range of 1 nm-100 μm, 1 nm-1 μm, 1-200 nm, or 1-100 nm.

Additionally or alternatively, the coating may have a thickness in the range of 100 nm-1 μm, 100-500 nm, or 100-300 nm. These ranges may provide the advantage of having a more predictable performance as a nanoscale thickness of below 100 nm is avoided.

Additionally or alternatively, the coating may have a thickness in the range of 1-20 μm, 3-15 μm, or 5-10 μm. These ranges may have the advantage of ensuring a good durability of the coating.

Additionally or alternatively, the thickness of the coating may have a tolerance of ±1000 nm, ±100 nm, ±10 nm, or ±1 nm.

Additionally or alternatively, a longitudinal extent of the side wall portion may be equal to or greater than a diameter of the distal end wall portion. The wall may be cylindrically shaped and/or cup-shaped and/or pot-shaped.

This disclosure also relates to an endoscope which may comprise:

a distal tip with a tip housing according to any of the previous claims;

a handle with a handle housing for gripping and a control member, e.g. a control lever;

an insertion tube for insertion into a patient, the insertion tube extending between the handle housing and the distal tip, and having a bending section positioned adjacent to the distal tip;

one or more steering wires connecting the control member with the bending section, the control member being rotatable around a pivot axis to effect a bending movement of the bending section in one or more planes by tensioning the one or more steering wires; and a camera being positioned in the interior cavity of the tip housing and looking through the window portion, and optionally being electrically connected to the handle via one or more cables.

The tip housing may comprise a tip working channel portion being in communication between a proximal entrance at a proximal end of the tip housing and a distal entrance at a distal end of the tip housing.

The tip working channel portion may form part of a working channel of the endoscope. The working channel may extend between the distal entrance of the tip working channel portion and a proximal port of the handle. The endoscope may be a disposable endoscope and may not be intended for being cleaned and/or sterilised after use.

A second aspect of this disclosure relates to a method for manufacturing a tip housing, optionally according to the first aspect of this disclosure, or an endoscope having a tip housing, optionally according to the first aspect of this disclosure, the method comprises the steps:

moulding at least one tip housing for an endoscope in a mould, preferably by injection moulding or by multi shot injection moulding, each tip housing comprising an integrally formed wall or an integrally moulded wall defining an interior cavity and a proximal opening providing access to the interior cavity, the wall comprising:

a longitudinally extending side wall portion, a distal end wall portion, and a window portion consisting essentially of a transparent first material and forming part of the side wall portion and/or the distal end wall portion; and a wall surface facing the exterior of the tip housing and having a window surface arranged exterior of the window portion and a distally facing end surface of the distal end wall portion; and applying a treatment formulation to provide a coating on at least the wall surface.

Additionally, the method may comprise a step of positioning the at least one tip housing in a treatment chamber, and the step of applying the treatment formulation to provide the coating on at least the wall surface may be performed in the treatment chamber.

Additionally or alternatively, the coating may be one or more selected coatings from the group consisting of: a transparent coating; a hydrophobic coating; a hydrophilic coating; an oleophobic coating; an oleophilic coating; and an optical coating, such as a notch filter coating, an infrared filter coating, an antireflection coating, a band stop/pass filter, and/or a low/high pass filter coating.

Additionally or alternatively, the coating may be applied on at least the window surface. This may provide the advantage of allowing tailoring of the surface characteristics of the window surface to suit the needs of the specific endoscopy application. Coating on the window surface may be advantageous for some or all the coatings of the disclosed coatings.

Additionally or alternatively, the treatment chamber may form part of a vapor deposition device. The treatment chamber may be defined by an enclosure of the vapor deposition device. The enclosure may comprise a sealable opening, which, when closed, seals treatment chamber in a liquid-tight and/or gas-tight manner. The vapor deposition device may perform the step of applying, in the treatment chamber, the treatment formulation, e.g. perfluorosilane, to vapor deposit, e.g. by chemical vapor deposition, a coating on at least the wall surface. The vapor deposition device may be a vapor deposition machine.

Additionally or alternatively, the coating may be applied by a dip coating process, a spray coating process, a vapor deposition process, or a painting process without requiring a treatment chamber.

Additionally or alternatively, the coating and/or treatment formulation comprises or consists essentially one or more selected from the group consisting of: silica-oxide, aluminum oxide, fluorocarbon, polytetrafluoroethylene (PTFE), hexamethyldisiloxane (HMDSO), perfluorosilane, and poly (p-xylylene).

Additionally or alternatively, the window surface may comprise a camera window surface configured to be positioned in front of a camera and allowing the camera to look through the camera window surface, and one or more illumination window surfaces, e.g. a first and a second illumination window surface, configured to be positioned in front of one or more light sources, respectively, e.g. a first and a second light source, such as LEDs, and allowing the one or more light sources to provide illumination for the camera through the one or more illumination window surface. The step of applying the treatment formulation to provide the coating, optionally a first coating, may comprise:

optionally positioning a first screening device to cover at least the one or more illumination window surfaces of the window surface prior to coating to prevent the one or more illumination window surfaces from being coated;

optionally applying, in the treatment chamber, the treatment formulation, optionally a first treatment formulation, to provide a first coating on the camera window surface, preferably while the one or more illumination window surfaces are covered by the first screening device;

optionally positioning a second screening device to cover at least the camera window surface of the window surface; and optionally applying, in the treatment chamber, the treatment formulation or a second treatment formulation, to provide a second coating on the one or more illumination window surfaces, preferably while the camera window surface is covered by the second screening device.

The first and second screening devices may be shaped so as provide the coating, e.g. first and second coatings, on 80% of the window surface of the distal end surface, and on less than 20% of the non-window surface of the distal end surface. The first and second coatings may be the same or they may be different. The first and second treatments may be the same or they may be different. This allows for providing a specific advantageous coating to the camera window surface and/or illumination window surface, but not to the remaining parts of the window surface.

Additionally or alternatively, the method may comprise the steps of:

positioning a third screening device to cover at least the window surface, the camera surface, or the illumination surface(s) prior to coating to prevent said surface from being coated;

applying, in the treatment chamber, the treatment formulation, optionally a third treatment formulation, to provide a coating, optionally a third coating, on the wall surface, preferably while the third screening device covers the respective surface(s);

This may be a particularly simple way of achieving most advantages of the coating, in particular when the coating is either the hydrophobic and/or oleophobic coating, or the hydrophilic and/or oleophilic coating.

Additionally or alternatively, the step of applying the treatment formulation to provide the coating, may comprise:

positioning a fourth screening device to cover at least the distal entrance of the tip working channel portion prior to coating to prevent coating of the tip working channel portion;

applying, in the treatment chamber, the treatment formulation, optionally a fourth treatment formulation, to provide a coating, optionally a fourth coating, on the camera window surface and/or the one or more illumination surfaces, preferably while the tip working channel portion is covered by the fourth screening device.

Additionally or alternatively, the window portion may comprise one or more internal illumination surfaces positioned opposite of the illumination window surfaces and an internal camera surface positioned opposite of the camera window surface. The coating may be a first coating. The method may comprise a step of applying a second, different coating, preferably prior to application of the first coating, on the one or more illumination window surfaces and/or the one or more internal illumination surfaces while other surfaces of the window portion may be screened to prevent the second coating from being applied to these other surfaces. The second coating may be a transmission scattering coating which may provide wide angle transmission scattering and/or narrow area transmission scattering. The amount of scattering may be measured by BS EN ISO 13468 using a hazemeter.

Additionally or alternatively, the step of positioning the tip housing in the treatment chamber may comprise the following steps of:

providing a jig having a treatment side and at least one hole or depression each with an opening on the treatment side;

positioning each tip housing in a separate hole of the jig so that the window surface of each tip housing is oriented towards the treatment side and/or protrudes from the opening on the treatment side of the jig so that the window surface is exposed for coating when the jig is positioned in the treatment chamber;

optionally arranging a first mandrel in a tip working channel portion of each tip housing;

optionally cleaning and/or preparing the window surface of each tip housing for coating; and positioning the jig including the at least one tip housing in the treatment chamber.

This may provide a particularly simple method of handling the tip housings prior and subsequent to coating thereof. Further, the jig may assist in restricting the coating area to the window surface and possibly some adjacent surfaces depending on the coating process. The first mandrel may prevent coating from being applied to at least some of interior surfaces of the tip working channel portion but allow coating to be applied to at least the window surface.

Additionally or alternatively, each hole or depression of the jig may be a mirror image of the proximal portion of the tip housing so as to ensure a correct orientation of each tip housing when placed in its respective hole of the jig. Each hole or depression of the jig may preferably include a mirror image of the partition wall of the tip housing. By ensuring a consistent orientation of the tip housing, the coating application on the desired surfaces is improved.

Additionally or alternatively, the first mandrel may form part of the jig. This may ensure a correct orientation of the tip housing, as the tip working channel portion is typically offset from a centre of the tip housing and thus may be advantageous for applying the coating to the desired surfaces.

Additionally or alternatively, the method may comprise positioning a second mandrel in the proximal opening of the tip housing to prevent internal surfaces of the tip housing from being coated in the application step(s). The second mandrel may form part of the jig and/or the first mandrel.

Additionally or alternatively, the mandrel(s) may be made of a metal, which may be particularly advantageous for a line of sight vapor deposition process, such as physical or plasma vapor deposition.

Additionally or alternatively, the first and/or second mandrel may be arranged together with a mandrel sealing element, e.g. an O-ring, preferably made of an elastomer, configured to seal the respective mandrel against the tip housing. This may allow for using a non-flexible mandrel in a chemical vapor deposition process, as the mandrel sealing element may prevent coating on non-intended surfaces. Further, such a mandrel sealing element may be easy to replace once worn out. For instance, the first and/or second mandrel may be made of a metal and the mandrel sealing element, e.g. an O-ring, may be made of an elastomer and be positioned in a recess of the respective mandrel to seal the mandrel against the tip housing. Such a mandrel sealing element is advantageous when a chemical vapor deposition process is used to prevent or reduce undesired coating of surfaces.

Additionally or alternatively, the mandrel(s) may be made of an elastomer, which may be particularly advantageous for a chemical vapor deposition process. The mandrel(s) may be configured to seal off the working channel when positioned therein.

Additionally or alternatively, the mandrel(s) may be one of the following: a cone, an extrusion, a plug, or a device configured for screening or sealing the tip working channel portion.

Additionally or alternatively, in the method of the second aspect of this disclosure, the window surface may instead be replaced by the surface to be coated, e.g. the entire window surface, the entire distal end surface, and/or the entire wall surface.

Additionally or alternatively, the step of cleaning and/or preparing the window surface may depend on the vapor deposition process, e.g. for a plasma-enhanced vapor deposition, the window surface may be plasma cleaned prior to the plasma-enhanced vapor deposition process, or for physical vapor deposition, any foreign matter on the surface to be coated may preferably be removed.

Additionally or alternatively, the step of moulding the tip housing may be performed in a mould, e.g. a single or multishot injection mould. The method may further comprise a step of automatically removing the moulded tip housing from the mould by a first automation device, e.g. a first robotic arm.

Additionally or alternatively, the step of applying a treatment formulation may comprise applying the treatment formulation by a vapor deposition process, such as chemical vapor deposition, physical vapor deposition, and/or plasma-enhanced vapor deposition. Plasma-enhanced may be advantageous for applying a coating on such a tip housing as the process temperature Additionally or alternatively, the method may comprise a step, optionally performed prior to the step of applying the treatment formulation, of:

evacuating air to provide a negative pressure relative to a surrounding pressure, optionally vacuum pressure, in the treatment chamber.

The absolute pressure in the treatment chamber may be less than $10^6$ Pa, $10^5$ Pa, $10^4$ Pa, $10^2$ Pa, $10^1$ Pa, or 1 Pa. The pressure in the treatment chamber relative to the surrounding pressure, e.g. outside the treatment chamber, may be less than 10%, 5%, 1%, 0.1%, 0.01%, or 0.001%.

Additionally or alternatively, the method may comprise a step of removing the coating from a portion of the wall, preferably adjacent to the proximal opening of the tip housing and preferably prior to assembling, e.g. adhesively, the tip housing to remaining parts of the endoscope. This may in some cases be more advantageous than screening the portion of the wall. The step may be performed by a corona discharge process.

Additionally or alternatively, the method may comprise a step of:

positioning a camera in the interior cavity of each coated tip housing to look through the window portion and out of the coated window surface.

Additionally or alternatively, the method may comprise a step, optionally performed after the step of positioning the camera in the interior cavity, of:

sealing the proximal opening of each coated tip housing with an adhesive to fluid-seal the interior cavity.

Additionally or alternatively, the method may comprise a step, optionally performed after the step of sealing the proximal opening, of:

assembling each coated tip housing in an endoscope.

Additionally or alternatively, the method may comprise a step, optionally performed after the step of assembling each tip housing in an endoscope, of:

sterilising each endoscope and coated tip housing.

Additionally or alternatively, the method may comprise a step, optionally performed after the step of sterilising, of:

packing each endoscope in a sterilised packaging.

This may prevent contaminants from contacting the endoscope.

A person skilled in the art will appreciate that any one or more of the above aspects of this disclosure and embodiments thereof may be combined with any one or more of the other aspects of this disclosure and embodiments thereof.

BRIEF DESCRIPTION OF THE DRAWINGS

Embodiments of this disclosure will be described in more detail in the following with regard to the accompanying figures. The figures show one way of implementing the present invention and are not to be construed as being limiting to other possible embodiments falling within the scope of the attached claim set.

FIG. 6b is a schematic illustration of a cross-section along lines C-C in FIG. 6a of the second jig with the second lid in a closed arrangement, FIG. 6c is a schematic illustration of a cross-section along lines C-C in FIG. 6a of a third jig with a third lid in a closed arrangement.

DETAILED DESCRIPTION OF THE INVENTION

Figures 1A, 1B:
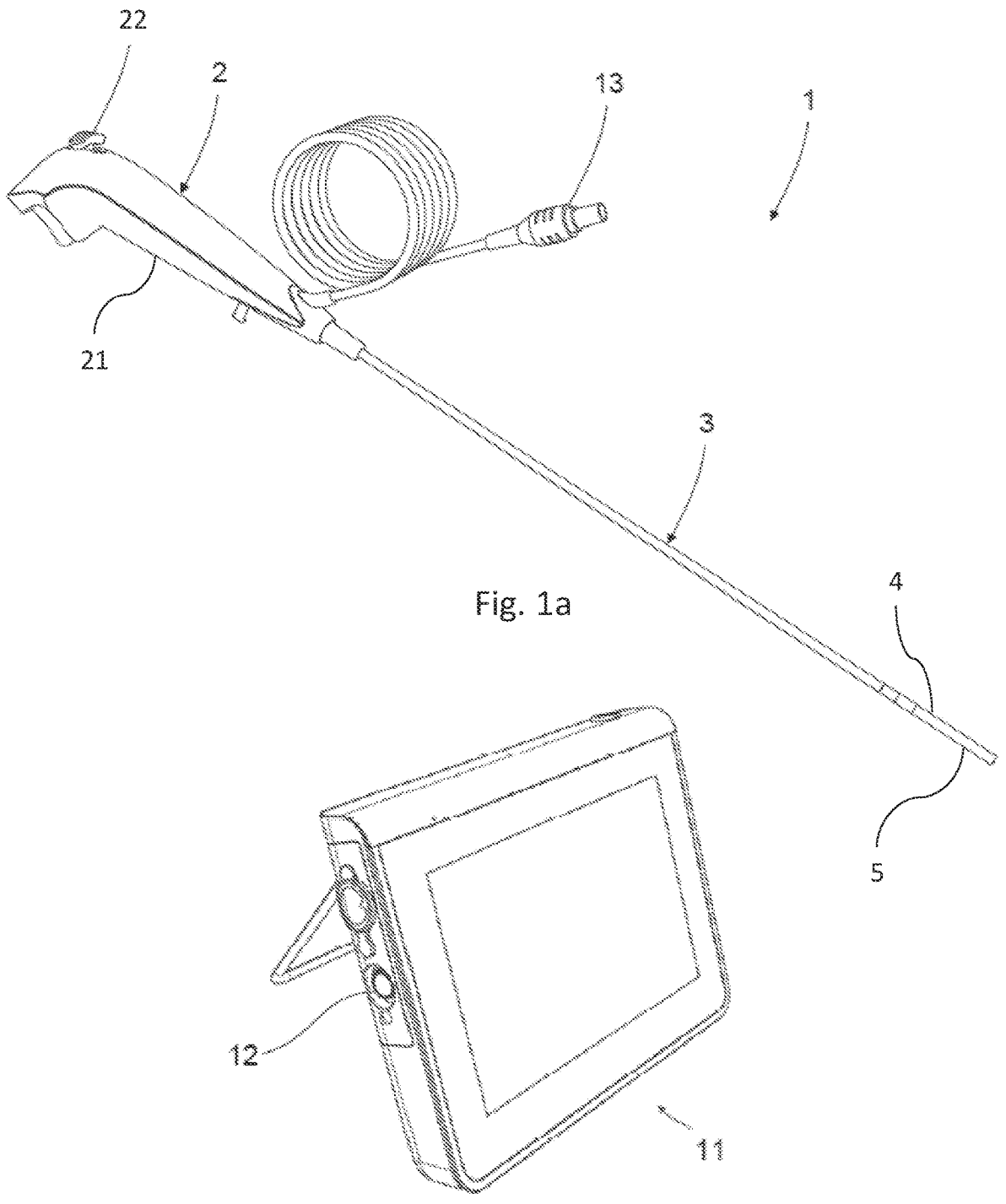
FIG. 1a is a schematic perspective view of an endoscope according to this disclosure.
FIG. 1b is a schematic perspective view of a monitor connectable to the endoscope of FIG. 1a, FIG. 2 is a schematic perspective view of a tip housing according to this disclosure.

FIG. 1a illustrates an endoscope 1 which is disposable, and not intended to be cleaned and reused. The endoscope 1 comprises a distal tip 5 with a tip housing 51; a handle 2 with a handle housing 21 for gripping and a control lever 22; an insertion tube 3 for insertion into a patient extending between the handle housing 21 and the distal tip 5 with a bending section 4 positioned proximal to the distal tip 5; two steering wires (not shown) connecting the control member with the bending section 4; and a camera (not shown) positioned in the tip housing 51 and looking through a window portion 70 of the tip housing 51 and out of a window surface 71 of the tip housing 51. The control member is rotatable around a pivot axis to effect a bending movement of the bending section in a single plane by tensioning either of the steering wires. The camera is electrically connected to a circuit (not shown) of the handle 2 via data and power cables.

In FIG. 1b, a monitor 11 is shown. The monitor 11 allows an operator to view an image captured by the camera assembly 8 of the endoscope 1. The monitor 11 comprises a cable socket 12 to which a monitor cable 13 of the endoscope 1 shown in FIG. 1a can be connected to establish a signal communication between the camera assembly 8 of the endoscope 1 and the monitor 11.

Figure 2:
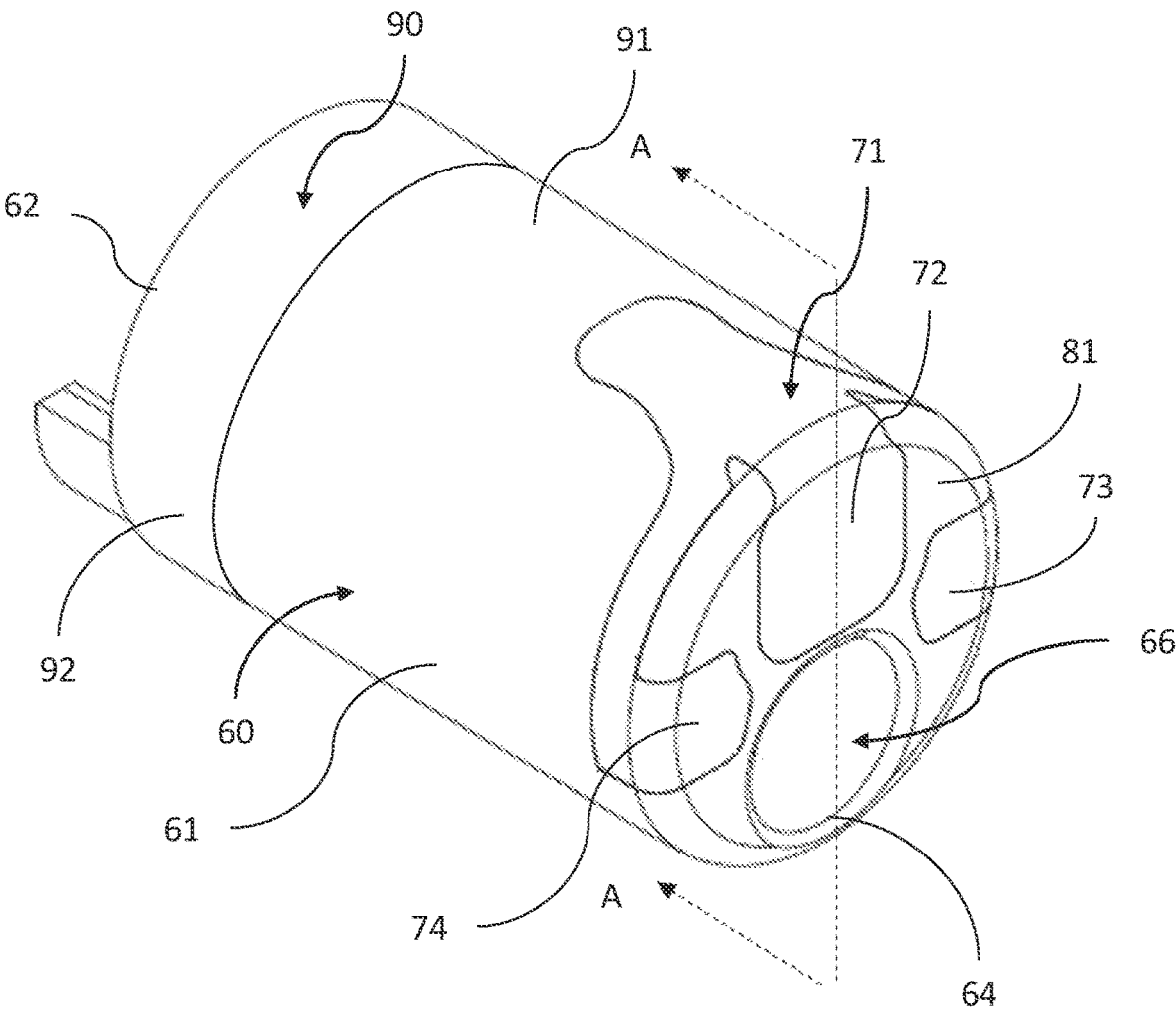
Figure 3:
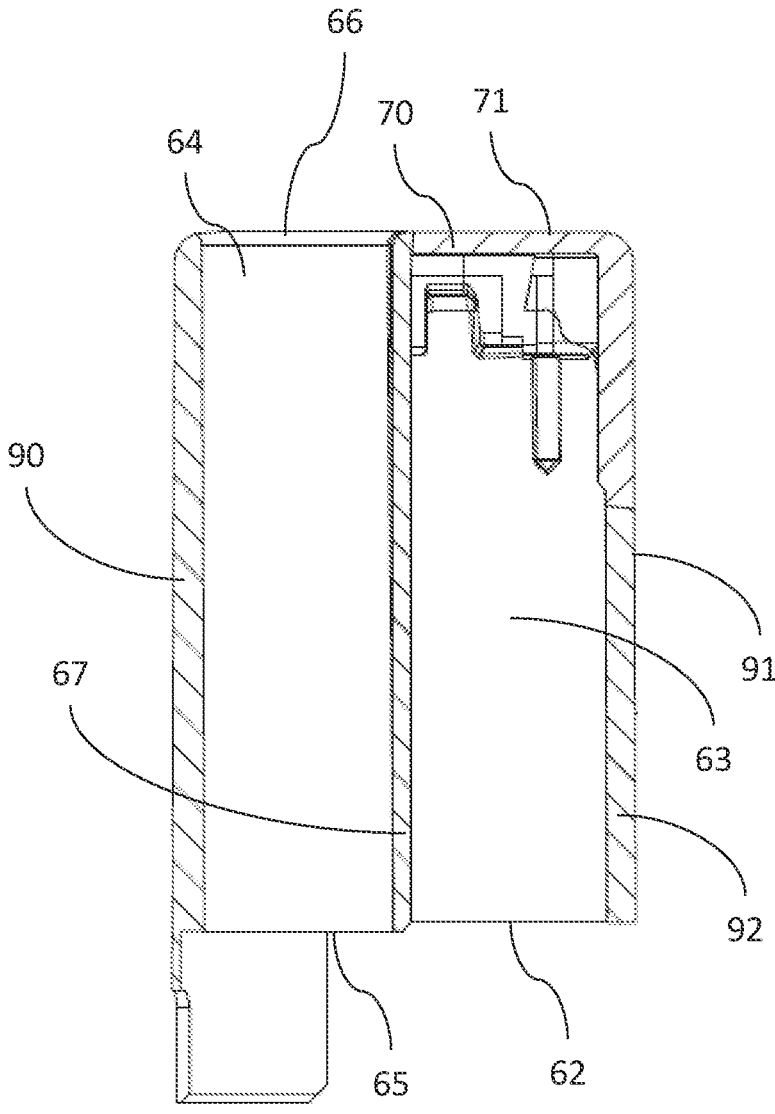
FIG. 3 is a schematic cross-sectional view of the tip housing along the lines A-A of FIG. 2.

FIGS. 2 and 3 illustrate the tip housing 51 of the endoscope 1 shown in FIG. 1a. The tip housing 51 comprises an integrally formed wall 60 defining an interior cavity 63 and a proximal opening 62 providing access to the interior cavity 63. The wall 60 is cylindrically cup-shaped or pot-shaped and comprises a longitudinally extending side wall portion 90, a window portion 70 consisting essentially of a transparent polymer material, and a distal end wall portion 80. The remaining portions of the wall other than the window portion 70 consists essentially of an opaque polymer material distinct from the transparent polymer material so that the wall consists essentially of the transparent polymer material and the opaque polymer material. The longitudinal extent of the side wall portion 90 is greater than the diameter of the distal end wall portion 80. The wall 60 further includes a wall surface 61 facing the exterior of the tip housing 51. The wall surface 61 comprises a side wall surface 91 of the side wall portion 90, a distally facing end surface 81 of the distal end wall portion 80, and a window surface 71 of the window portion 70. The window surface 71 comprises a side-facing portion forming part of the side wall surface 91 and a distally facing portion forming part of the distally facing end surface 81. The distally facing portion of the window surface 71 is divided into a camera window surface 72 configured to be positioned in front of the camera (not shown) allowing the camera to look through the camera window surface 72, a first illumination window surface 73 configured to be positioned in front of a first LED (not shown) of the distal tip allowing the first LED to provide illumination for the camera through the first illumination window 73, and a second illumination window surface configured to be positioned in front of a second LED of the distal tip allowing the second LED (not shown) to provide illumination for the camera through the second illumination window 74. The tip housing 51 comprises a tip working channel portion 64 extending between a proximal entrance 65 at a proximal end of the tip housing 51 and a distal entrance 66 at a distal end of the tip housing 51. A partition wall 67 of the tip housing 51 separates the tip working channel portion 64 from the interior cavity 63. The tip working channel portion 64 forms part of a working channel of the endoscope 1 which extends between the distal entrance 66 of the tip working channel portion 64 and a proximal port (not shown) of the handle 2.

The tip housing 51 comprises a coating covering the entire distal end surface 81, a distal portion of the side wall surface 91, and a distal portion of the tip working channel portion 64. A proximal portion 92 of the tip housing 51 is thus uncoated, the border of the coated portion and the uncoated portion is shown on FIG. 2 as the circumferential line adjacent to the 92 reference numeral. In practice the border may not be exactly sharp but may be a transition over a length of the tip housing 52. The coating is a transparent, hydrophobic, oleophobic coating.

Figures 4A, 4B, 4C:
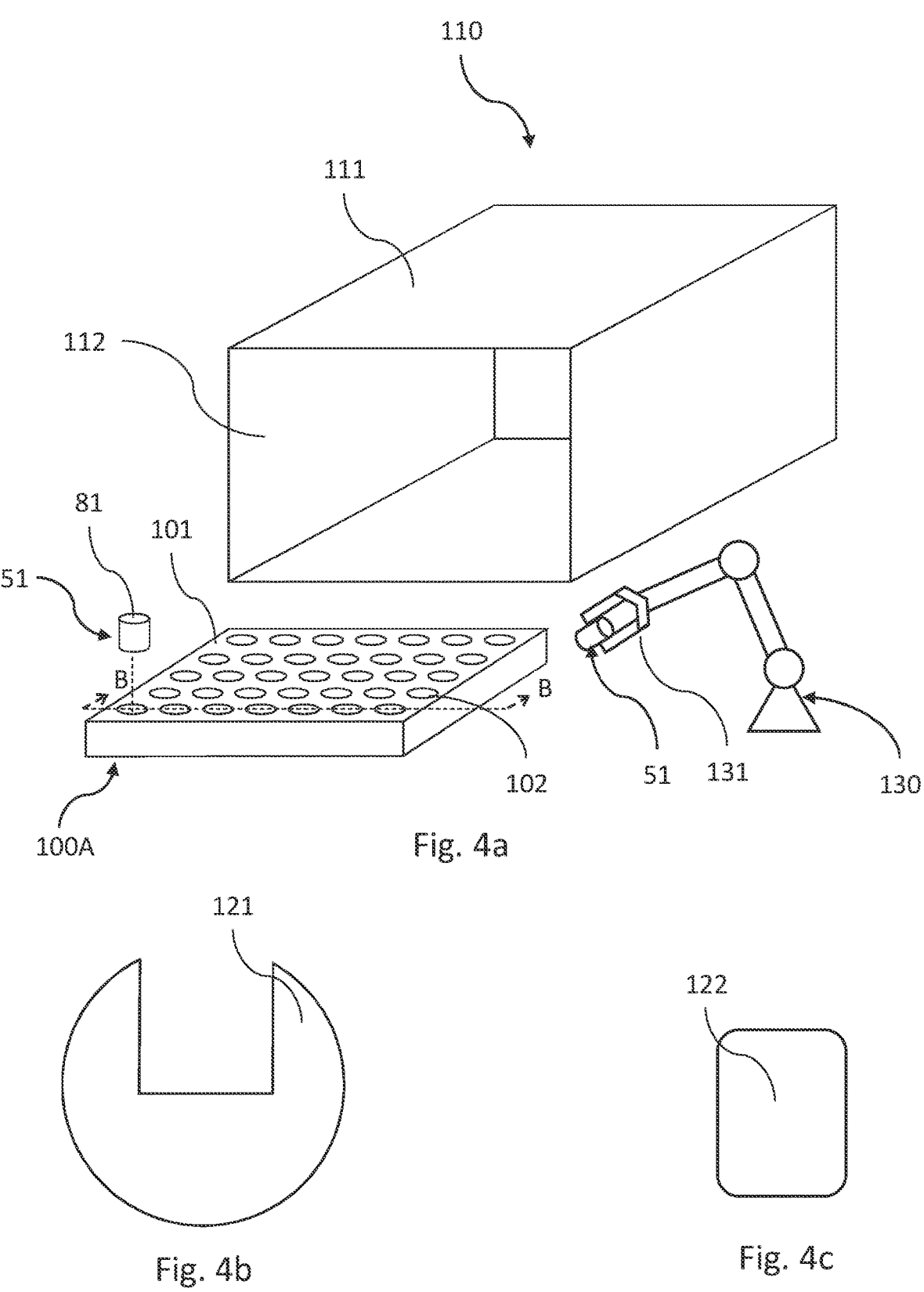
FIG. 4a is a schematic perspective view of a treatment arrangement including a first jig for the coating method according to this disclosure.
FIG. 4b is a schematic illustration of a first screening device.
FIG. 4c is a schematic illustration of a second screening device.

As illustrated in FIG. 4a, such a tip housing 51 can be manufactured and assembled with the remaining parts of the endoscope 1 in a first embodiment by a method comprising the following steps:

First, moulding a plurality of the tip housing 51 by a two-component injection moulding process, so that each tip housing 51 comprises an integrally formed wall 60 defining an interior cavity 63 and a proximal opening 52 providing access to the interior cavity, the wall 60 comprising:

the longitudinally extending side wall portion 90, and the distal end wall portion 90 including the window portion 70, which consists essentially of a transparent polymer material; and the wall surface 61 facing the exterior of the tip housing 51 and having the distally facing end surface 81 of the distal end wall portion 80, which includes the window surface 71 of the window portion 70.

Second, providing a first jig 100A having a treatment side 101 and a plurality of holes 102, each with an opening on the treatment side 101.

Third, positioning each tip housing 51 in a separate hole 102 of the first jig 100A so that the window surface 71 of each tip housing 51 is oriented towards the treatment side 101 or protrudes from the hole opening on the treatment side 101 of the first jig 100A. This step is performed by an automation device 130, e.g. a pick and place robotic arm, with an end effector 131 picking each tip housing 51 and placing it in its respective hole 102 of the first jig 100A. The automation device 130 may pick each tip housing 51 directly from the mould after injection moulding thereof or may pick each tip housing 51 from a different container.

Figure 5:
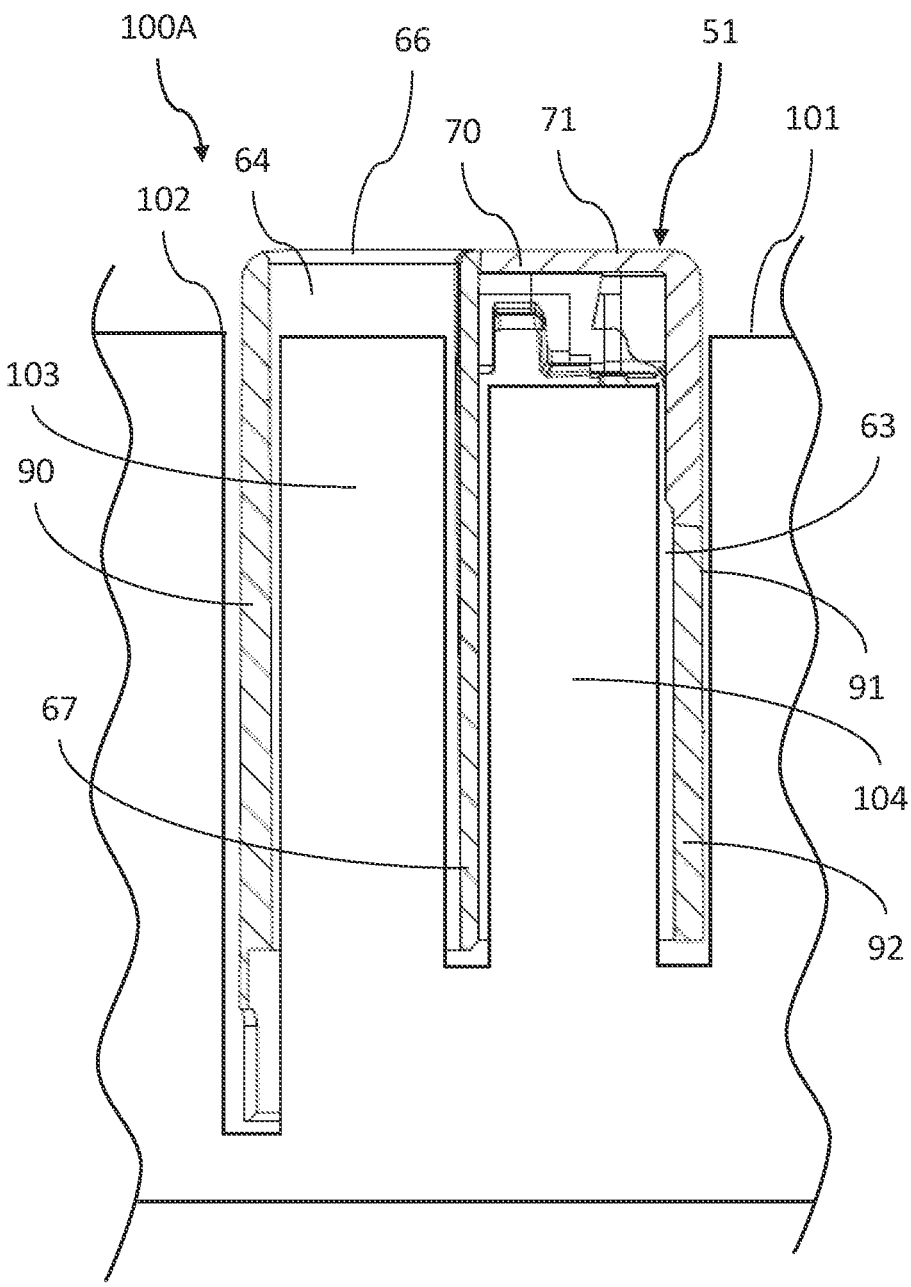
FIG. 5 is a schematic detail illustration of a cross-section along lines B-B of FIG. 4a of a first jig of the treatment arrangement of FIG. 4a, FIG. 6a is schematic perspective illustration of a second jig with a second lid in an open arrangement.

Fourth, arranging a first cylindrical mandrel 103 in the tip working channel portion 64 of each tip housing 51 as best seen in FIG. 5. The first mandrel 103 has an outer diameter matching the inner diameter of the tip working channel portion 64. The first mandrel 103 is made of a metal, which is advantageous for a high temperature plasma vapor deposition process. Alternatively, the first mandrel 103 is made of an elastomer sealing against the tip working channel portion 64, which is advantageous for a chemical vapor deposition process. As best seen in FIG. 5, the first mandrel 103 is integrally formed with the first jig 100A and thus protrudes upright from the bottom of each hole 102. Placing the tip housing 51 on the first mandrel 103 ensures that the tip housing 51 is correctly oriented for subsequent coating. Correspondingly, a second mandrel 104 is arranged in the interior cavity 63. The second mandrel 104 has an outer crescent-shaped circumference matching an inner crescent-shaped circumference of the interior cavity 63.

Fifth, preparing and cleaning the window surface 71 of each tip housing 51 for coating by plasma cleaning.

Sixth, positioning the first jig 100A including the plurality of tip housings 51 in a treatment chamber 112 defined by an enclosure 111 of a vapor deposition machine 110.

Seventh, sealing the enclosure 111 gas-tight and evacuating air from the treatment chamber 112 via a pump to provide a negative pressure relative to a surrounding pressure of in the treatment chamber 112.

Eighth, applying to each tip housing 51 in the treatment chamber 112 a treatment formulation comprising hexamethyldisiloxane (HMDSO) by low-pressure plasma-enhanced chemical vapor deposition to provide a transparent, hydrophobic, and oleophobic coating of fluorocarbon on the entire distal end surface 81 including the entire window surface 71 and the distal portion of the side wall surface 91, alternatively, this step may comprise applying to each tip housing 51 in the treatment chamber 112 a treatment formulation comprising by chemical vapor deposition to provide a transparent, hydrophobic, and oleophobic coating of perfluorosilane on the entire distal end surface 81 including the entire window surface 71 and the distal portion of the side wall surface 91.

Ninth, removing the first jig 100A including the plurality of the tip housings 51 from the treatment chamber 112.

Tenth, positioning a camera in the interior cavity 63 of each tip housing 51 so that the camera looks through the window portion 70 and out of the coated window surface 71.

Eleventh, sealing the proximal opening 62 of each tip housing 51 with an adhesive to fluid-seal the interior cavity 63.

Twelfth, assembling each tip housing 51 in an endoscope 1 by connecting the proximal end of the tip housing 51 with the bending section 4 of the endoscope 1.

Thirteenth, sterilising each endoscope 1 and coated tip housing 51.

Fourteenth, packing each endoscope 1 in a sterilised packaging (not shown).

In a second and third embodiment, the window surface 71 comprises a camera window surface 72 configured to be positioned in front of a camera of the endoscope and allowing the camera to look through the camera window surface 72, and a first 73 and a second illumination window surface 74 configured to be positioned in front of a first and a second LED light source of the endoscope 1, respectively and allowing the two LED light sources to provide illumination for the camera through the first and second illumination window surfaces 73, 74, wherein step eight above is, in the second embodiment, replaced by the following steps:

positioning a first screening device 121, as best seen in FIG. 4b, to cover the entire first and second illumination window surfaces 73, 74 of the window surface 71 to prevent the first and second illumination window surfaces 73, 74 from being coated;

applying, in the treatment chamber 112, a first treatment formulation comprising hexamethyldisiloxane (HMDSO) to provide a first coating comprising fluorocarbon by low-pressure plasma vapor deposition to provide a transparent, optical filter, hydrophobic, and oleophobic coating on the entire camera window surface 72 but not on the illumination window surfaces 73, 74;

positioning a second screening device 122, as best seen in FIG. 4c, to cover the entire camera window surface 72 of the window surface 71; and applying, in the treatment chamber 112, a second treatment formulation comprising hexamethyldisiloxane (HMDSO) to provide a second coating comprising fluorocarbon by flow-pressure plasma vapor deposition to provide a transparent, hydrophobic, and oleophobic coating on the entire first and second illumination window surfaces 73, 74 but not on the camera window surface 72.

In the third embodiment, the steps of the second embodiment are replaced by the following steps:

positioning a first screening device 121, as best seen in FIG. 4b, to cover the entire first and second illumination window surfaces 73, 74 of the window surface 71 to prevent the first and second illumination window surfaces 73, 74 from being coated;

applying, in the treatment chamber 112, a first treatment formulation to provide a first coating comprising perfluorosilane by chemical vapor deposition to provide a transparent, optical filter, hydrophobic, and oleophobic coating on the entire camera window surface 72 but not on the illumination window surfaces 73, 74;

positioning a second screening device 122, as best seen in FIG. 4c, to cover the entire camera window surface 72 of the window surface 71; and applying, in the treatment chamber 112, a second treatment formulation to provide a second coating comprising perfluorosilane by chemical vapor deposition to provide a transparent, hydrophobic, and oleophobic coating on the entire first and second illumination window surfaces 73, 74 but not on the camera window surface 72.

A fourth embodiment is illustrated in FIGS. 6a and 6b involving a second jig 100B and a second lid 120B. The second jig 100B comprises a plurality of holes 102 (of which only one is shown), each comprising a first mandrel 103 provided in the same way as shown in FIG. 5 but omitting the second mandrel 104.

The second lid 120B comprises a plurality of openings 124 (of which only one is shown) matching the number of the plurality of holes 102 of the second jig 100B. In this fourth embodiment, a fourth screening device 123 forms part of the second lid 120B and is adjacent to each opening 124. Prior to placing the second jig 100B in the treatment chamber, the second lid 120B is placed on top of the second jig 100B to partially cover the distal entrance 66 of the tip working channel portion 64 of each tip housing 51 in the plurality of holes 102 of the second jig 100B. The tip housings are then coated in the same way as previously described.

A fifth embodiment is illustrated in FIG. 6c involving a third jig 100C and a third lid 120C corresponding essentially to the second jig 100B and the second lid 120B only differing in that the first mandrel 103 is omitted, the third jig 100C is provided with first jig mating elements 108 in the form of female mating depressions in the treatment side 101, and the third lid 100C is provided with first lid mating elements 128 in the form of male mating protrusions for mating with the first jig mating elements 108. The tip housings are coated in the same way as previously described.

Figures 7A, 7B:
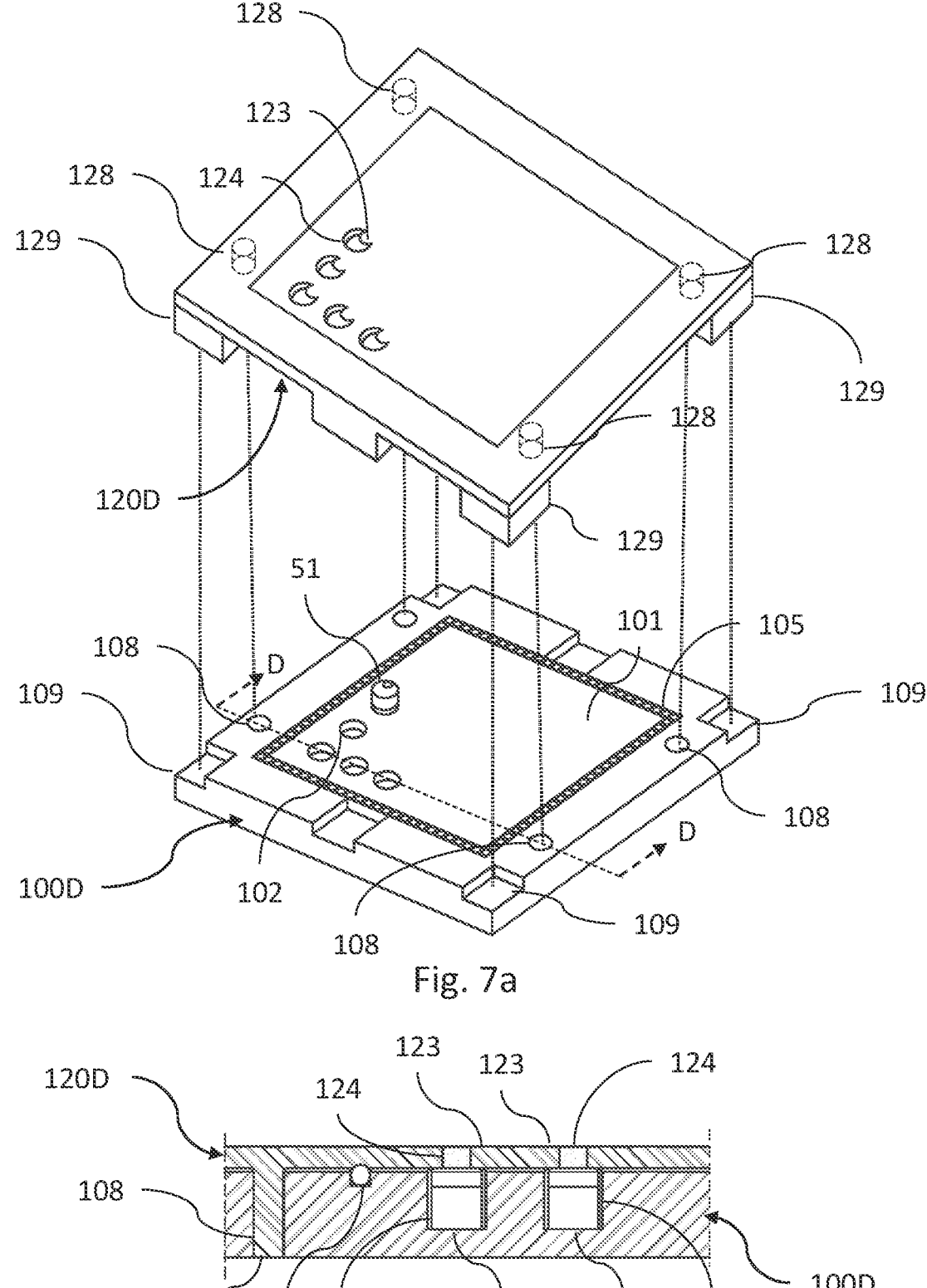
FIG. 7a is a schematic perspective illustration of a fourth jig with a fourth lid in an open arrangement.
FIG. 7b is a schematic illustration of a cross-section along lines D-D in FIG. 7a of the third jig with the third lid in a closed arrangement.

A sixth embodiment is illustrated in FIGS. 7a and 7b involving a fourth jig 100D and a fourth lid 120D comprising the features of the third jig 100C and the third lid 120C. The fourth jig 100D further comprises a sealing element 105 extending along an outer perimeter enclosing the plurality of holes 102 of the fourth jig 100D. In addition to the first jig mating elements 108 and lid mating elements 128 (which are provided as in the fifth embodiment), second jig female mating elements 109 and corresponding second lid male mating elements 129 are provided at the perimeter of the fourth jig 100D and the fourth lid 120D. The tip housings are coated in the same way as previously described.

Any of the screening devices (i.e. the first screening device 121, the second screening device 122, the third screening device, or the fourth screening device 123) may be employed in all disclosed embodiments depending on the desired coated and uncoated surfaces. For instance, the first screening device may be employed when no coating is desired on the illumination surfaces, the second screening device when no coating is desired on the camera window surface, and the fourth screening device 123 when no coating is desired on or in the tip working channel portion. Advantageously, the same tip housings can have different surfaces coated by subjecting them to a sequence of coating processes as described above, wherein a different type of screening device is used in each coating process.

LIST OF REFERENCES

The following is a list of reference numerals used throughout this disclosure. In case of any doubt, the reference numerals of the following list apply.

| | |
|---|---|
| 1 | endoscope |
| 11 | monitor |
| 12 | cable socket |
| 13 | monitor cable |
| 2 | handle |
| 21 | handle housing |
| 22 | control lever |
| 3 | insertion tube |
| 4 | bending section |
| 5 | distal tip |
| 51 | tip housing |
| 60 | wall |
| 61 | wall surface |
| 62 | proximal opening |
| 63 | interior cavity |
| 64 | tip working channel portion |
| 65 | proximal entrance |
| 66 | distal entrance |
| 67 | partition wall |
| 70 | window portion |
| 71 | window surface |
| 72 | camera surface |
| 73 | first illumination surface |
| 74 | second illumination surface |
| 80 | distal end wall portion |
| 81 | distal end surface |
| 90 | side wall portion |
| 91 | side wall surface |
| 92 | proximal portion |
| 100 | jig |
| 101 | treatment side |
| 102 | hole |
| 103 | first mandrel |
| 104 | second mandrel |
| 105 | sealing element |
| 108 | first jig mating element |
| 109 | second jig mating element |
| 110 | vapor deposition machine |
| 111 | enclosure |
| 112 | treatment chamber |
| 120 | lid |
| 121 | first screening device |
| 122 | second screening device |
| 123 | fourth screening device |
| 124 | opening |
| 128 | first lid mating element |
| 129 | second lid mating element |
| 130 | automation device |
| 131 | end effector |

The invention claimed is:

1. A method for manufacturing endoscopes, the method comprising:

injection moulding tip housings in a two-component injection polymer moulding process, each of the tip housings being molded from polymers, the two component injection molding process comprising injection moulding a first component comprising a first material and subsequently injection molding a second component comprising a second material, the second component forming a liquid tight border with the first component to form the tip housing, the first material being transparent and the second material being opaque, each of the tip housings comprising an interior cavity and a proximal opening providing access to the interior cavity, the second component comprising:

a longitudinally extending side wall portion, and a distal end wall portion, and the first component comprising:

a window portion bonded to the side wall portion and/or the distal end wall portion, the window portion having a window surface including a camera window surface and an illumination window surface, the distal end wall portion and the window portion forming a distally facing end surface;

placing the tip housings in holes of a jig having a treatment side and a mandrel in each of the holes, each of the mandrels positioned in the interior cavity of each of the tip housings after the tip housings are placed in the holes, and each of the distally facing end surfaces being exposed on the treatment side of the jig;

covering the illumination window surfaces with a first mask configured to expose the camera window surfaces; and coating the camera window surfaces with a first treatment formulation.

2. A method according to claim 1, the method further comprising:

before covering the illumination window surfaces with the first mask or after coating the camera window surfaces with the first treatment formulation, covering the camera window surfaces with a second mask configured to expose the illumination window surfaces; and coating the illumination window surfaces with a second treatment formulation.

3. A method according to claim 1, wherein coating the camera window surfaces comprise placing the jig in a treatment chamber of a vapor deposition device, and wherein coating the camera window surfaces with the first treatment formulation comprises applying, by vapor deposition, the first treatment formulation.

4. A method according to claim 1, wherein each of the tip housings comprises a tip working channel portion, and wherein the mandrels are positioned in the tip working channel portions.

5. A method according to claim 4, wherein a mandrel sealing element is arranged together with each of the mandrels to seal the first mandrels against the tip housings.

6. A method according to claim 1, wherein the injection moulding of the tip housings is performed in a mould, and the method further comprises:

automatically removing the tip housings from the mould by a first automation device, and automatically placing the tip housings, after said removing and by a second automation device, in the holes of the jig by a second automation device.

7. A method according to claim 6, wherein the first automation device is the same as the second automation device.

8. A method according to claim 1, wherein, for each of the tip housings, the camera window surface is configured to be positioned in front of a camera of the endoscope, and the illumination window surface is configured to be positioned in front of a light source of the endoscope.

9. A method according to claim 3, further comprising:

positioning a third screen to cover at least the window surfaces prior to said coating to prevent the window surfaces from being coated; and applying, in the treatment chamber, a third treatment formulation, to provide a coating on the wall surfaces.

10. A method according to claim 9, wherein each of the tip housings comprises a tip working channel portion having a distal entrance at the distal end wall portion of the tip housing, the method further comprising:

positioning a fourth screen to cover at least the distal entrances of the tip working channel portions to prevent coating of the tip working channel portions.

11. A method according to claim 1, further comprising:

inserting, in each of the tip housings, a camera proximally of and longitudinally aligned with the camera window surface and a light source proximally of and longitudinally aligned with the illumination window surface;

attaching each of the tip housings to respective insertion cords of the endoscopes; and packaging each of the endoscopes in respective sterilized packagings.

12. A method according to claim 2, wherein the second treatment formulation is the same as the first treatment formulation.

13. A method according to claim 1, wherein each of the tip housings comprises a tip working channel portion, and wherein the jig comprises, in each of the holes, a second mandrel, each of the mandrels positioned in a respective camera cavity of the tip housing and each of the second mandrels positioned in a respective tip working channel portion of the tip housing.

* * * * *